United States Patent [19]

Shirahata

[11] Patent Number: 4,845,238
[45] Date of Patent: Jul. 4, 1989

[54] EPOXY GROUP CONTAINING DISILAZANE AND METHOD FOR ITS PRODUCTION

[75] Inventor: Akihiko Shirahata, Chiba, Japan

[73] Assignee: Toray Silicone Co., Ltd., Tokyo, Japan

[21] Appl. No.: 101,891

[22] Filed: Sep. 28, 1987

[30] Foreign Application Priority Data

Oct. 30, 1986 [JP] Japan .................................. 61-259554

[51] Int. Cl.[4] .............................................. C07F 7/10
[52] U.S. Cl. ...................................... 549/215; 556/412
[58] Field of Search .......................... 549/215; 556/412

[56] References Cited

U.S. PATENT DOCUMENTS

| | | | |
|---|---|---|---|
| 2,721,873 | 10/1955 | MacKenzi et al. | 556/412 |
| 2,823,218 | 2/1958 | Speier et al. | 556/412 |
| 3,296,291 | 1/1967 | Chalk et al. | 556/412 |
| 3,567,755 | 3/1971 | Seyfried et al. | 549/215 |
| 3,631,086 | 12/1971 | Seyfried et al. | 549/215 |
| 3,714,212 | 1/1973 | Lengnick | 556/412 |
| 4,417,068 | 11/1983 | Kollmeier et al. | 549/215 |

FOREIGN PATENT DOCUMENTS 834326 5/1960 United Kingdom ................ 549/215

OTHER PUBLICATIONS

E. P. Plueddemann et al., Jour. Am; Chem. Soc., vol. 81 (1959), pp. 2632-2635.

Primary Examiner—Glennon H. Hollrah
Assistant Examiner—A. A. Owens
Attorney, Agent, or Firm—Donald M. MacKay

[57] ABSTRACT

An epoxy group-containing disilazane having the formula,

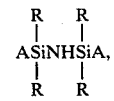

wherein A is

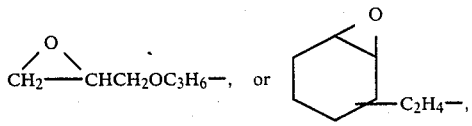

is described. Also described is a process for producing the epoxy group-containing disilazane. The process comprises reacting a disilazane having the formula,

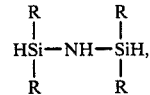

with an epoxy compound selected from a group consisting of allyl glycidyl ether and vinylcyclohexene oxide in the presence of a platinum-type catalyst.

7 Claims, No Drawings

EPOXY GROUP CONTAINING DISILAZANE AND METHOD FOR ITS PRODUCTION

BACKGROUND OF THE INVENTION

This invention relates to a novel epoxy group-containing disilazane. In addition, this invention relates to a method for producing the epoxy group-containing disilazane.

Gamma-glycidoxypropyltimethoxysilane and beta-(3,4-epoxycyclohexyl)ethyltrimethoxysilane are known in the art as epoxy group-containing organosilanes and are used as epoxy-substituted organosilylating agents. However, neither epoxy group-containing disilazanes nor a method for their production are known at present.

The object of the present invention is to provide both epoxy group-containing disilazanes and a method for their production.

DESCRIPTION OF THE INVENTION

In accordance with the instant invention, there is provided an epoxy group-containing disilazane. What is described, therefore is an epoxy group-containing disilazane having the formula, $$\begin{array}{c} R \quad R \\ | \quad | \\ ASiNHSiA, \\ | \quad | \\ R \quad R \end{array}$$

wherein R is a monovalent hydrocarbon group, and A is

 or 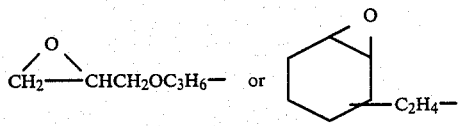

The monovalent hydrocarbon group, R, is exemplified by an alkyl group such as methyl, ethyl, propyl, and octyl; substituted alkyl group such as 2-phenylethyl, 2-phenylpropyl, or 3,3,3-trifluoropropyl; an aryl group such as phenyl and; a substituted aryl group such as tolyl.

The epoxy group-containing disilazane of the invention is concretely exemplified by

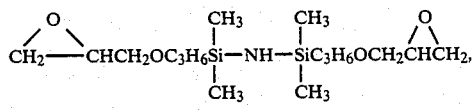

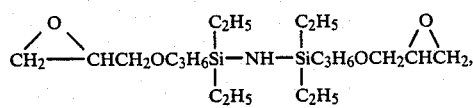

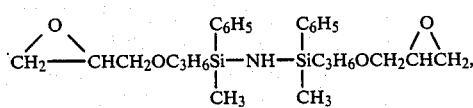

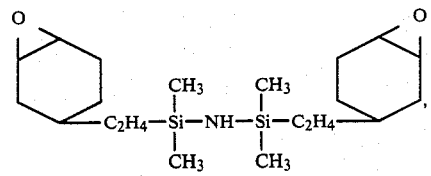

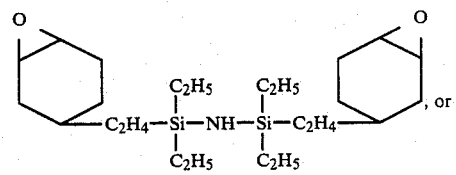

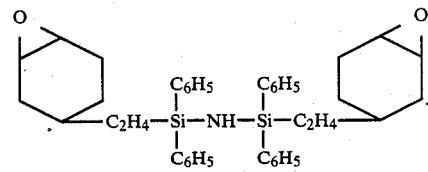

The epoxy group-containing disilazane of the instant invention finds utility as a silylating agent for various organic compounds and organosilicon compounds, as well as an organosilylating agent for solid substrates.

The instant invention also provides for a process for the production of an epoxy group-containing disilazane. What is described, therefore, is process for producing an epoxy group-containing disilazane, said process comprising reacting a disilazane having the formula, $$\begin{array}{c} R \quad R \\ | \quad | \\ HSi-NH-SiH, \\ | \quad | \\ R \quad R \end{array}$$

with an epoxy compound selected from a group comprising allyl glycidyl ether and vinylcyclohexene oxide in the presence of a platinum-type catalyst; where R is a monovalent hydrocarbon group.

The disilazane is concretely exemplified by

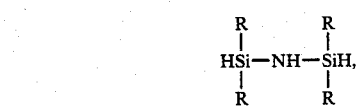

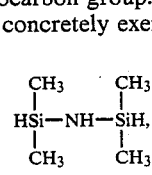

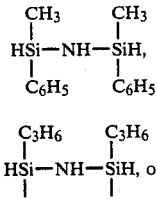

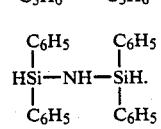

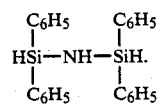

Platinum-type catalysts operative in the present invention are exemplified by finely divided platinum, finely divided platinum adsorbed on a carbon powder support, chloroplatinic acid, alcohol-modified chloroplatinic acid, olefin complexes of chloroplatinic acid, chloroplatinic acid-vinylsiloxane coordination compounds, platinum black, palladium and rhodium. The quantity of use of the platinum-type catalyst will vary with the type of catalyst used, and so cannot be specifically restricted. However, it is preferably in a range from about 0.1 to 1,000 ppm as platinum-type metal proper based on the weight of the disilazane.

The reaction temperature is not specifically restricted, but is preferably in a range from about 20° C. to 300° C.

The atmosphere in the reaction system also is not specifically restricted, and can be air or an inert gas, at ambient pressure or under elevated pressure.

The simultaneous use is also permissible of an aromatic hydrocarbon solvent such as benzene, toluene or xylene; a ketone solvent; or a chlorinated hydrocarbon solvent.

So that those skilled in the art may better understand and appreciate the instant invention, the following examples are presented. The examples are presented as being illustrative and are not to be construed as limiting the claims as delineated herein.

EXAMPLE 1

27.4 g (0.24 mole) of allyl glycidyl ether was placed in a 100 ml four-neck flask equipped with a thermometer, stirrer, reflux condenser, and addition funnel. A vinylsiloxane complex of chloroplatinic acid was then added to give 50 ppm as platinum metal proper based on the tetramethyldisilazane whose addition followed. After heating to 140° C., 13.4 g (0.1 mole) of tetramethyldisilazane was gradually dripped in with stirring. The vigorous evolution of heat was observed during this addition. After addition, stirring was continued at 140° C. for 30 minutes, followed by distillation in vacuo to afford 32 g of a fraction at 170° C./2 mmHg.

The results of elemental analysis, nuclear magnetic resonance analysis, and infrared absorption spectral analysis confirmed the product to be a compound having the formula, $$\underset{CH_2}{\overset{O}{\diagdown}}\!\!-\!\!CHCH_2OC_3H_6\underset{\underset{CH_3}{|}}{\overset{\overset{CH_3}{|}}{Si}}\!-\!NH\!-\!\underset{\underset{CH_3}{|}}{\overset{\overset{CH_3}{|}}{Si}}C_3H_6OCH_2CHCH_2\overset{O}{\diagdown}\!.$$

Known methods of elemental analysis were used to determine carbon, hydrogen, and nitrogen content of the product. The following is a comparison of the analysis and the calculated content of these elements:

Analyses: C=53.30%, H=9.81%, N=3.78%. Calculations: C=53.14%, H=9.76%, N=3.87%.

The results of nuclear magnetic resonance analysis ($\delta$ ppm) were:
 0.15 (s, 12H)
 0.43~0.80 (m, 4H)
 1.05 (broad s, 1H)
 1.40~2.00 (m, 4H)
 2.45~2.88 (m, 4H)
 2.90~3.20 (m, 2H)
 3.20~3.86 (m, 8H)

The results of infrared absorption spectral analysis (cm$^{-1}$) were: 3300, 3030, 2980, 2940, 2920, 2850, 1340, 1260, 1170, 1095, 930, 835, 790.

EXAMPLE 2

29.8 g (0.24 mole) of vinylcyclohexene oxide was placed in a 100 ml four-neck flask equipped with a thermometer, stirrer, reflux condenser, and addition funnel. To this was added 2 weight percent isopropanolic chloroplatinic solution sufficient to give 50 ppm as platinum metal proper based on the tetramethyldisilazane whose addition followed. After heating to 140° C., 13.4 g (0.1 mole) of tetramethyldisilazane was gradually dripped in with stirring. The vigorous evolution of heat was observed during this addition. After addition, heating was continued for 30 minutes at 140° C. with stirring, followed by distillation in vacuo to obtain 34 g of a fraction at 145° C./0.3 mmHg.

The results of elemental analysis, nuclear magnetic resonance analysis, and infrared absorption spectral analysis confirmed the product to be a compound having the formula, $$\underset{}{\overset{O}{\diagup}}\!\!\diagdown\!\!-\!\!C_2H_4\!-\!\underset{\underset{CH_3}{|}}{\overset{\overset{CH_3}{|}}{Si}}\!-\!NH\!-\!\underset{\underset{CH_3}{|}}{\overset{\overset{CH_3}{|}}{Si}}\!-\!C_2H_4\!-\!\underset{}{\diagdown\!\!\overset{O}{\diagup}}$$

Known methods of elemental analysis were used to determine carbon, hydrogen, and nitrogen content of the product. The following is a comparison of the analysis and the calculated content of these elements:

Analyses: C=62.99%; H=10.28%; N=4.38%. Calculations: C=62.93%; H=10.30%; N=4.46%

The results of nuclear magnetic resonance analysis ($\delta$ ppm) were:
 0.15 (s, 12H)
 0.40~0.75 (m, 4H)
 1.00~2.40 (m, 19H)
 2.80~3.10 (broad s, 4H)

The results of infrared absorption spectral analysis (cm$^{-1}$) were: 3300, 3010, 2980, 2920, 2850, 1320, 1260, 1175, 1090, 920, 840.

What is claimed is:

1. An epoxy group-containing disilazane having the formula, $$\underset{R}{\overset{R}{\underset{|}{|}}}\!ASiNHSiA,\underset{R}{\overset{R}{\underset{|}{|}}}$$

wherein each R is independently selected and is lower alkyl and pheyl group, and A is $$\underset{CH_2}{\overset{O}{\diagup}}\!\!\diagdown\!\!-\!\!CHCH_2OC_3H_6\!-\quad \text{or} \quad \underset{}{\diagdown\!\!\overset{O}{\diagup}}\!\!-\!\!C_2H_4\!-\!$$

2. An epoxy group-containing disilazane, according to claim 1, wherein A is $$\underset{CH_2}{\overset{O}{\diagup}}\!\!\diagdown\!\!-\!\!CHCH_2OC_3H_6-,$$

each R is a methyl group, and the epoxy group-containing disilazane has the formula,

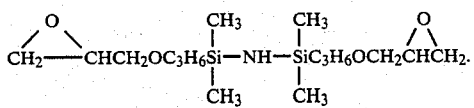

3. An epoxy group-containing disilazane, according to claim 1, wherein A is

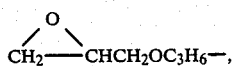

each R is an ethyl group, and the epoxy group-containing disilazane has the formula,

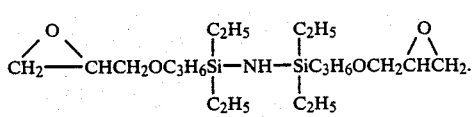

4. An epoxy group-containing disilazane, according to claim 1, wherein A is

each R is a methyl group or a phenyl group, and the epoxy group-containing disilazane has the formula,

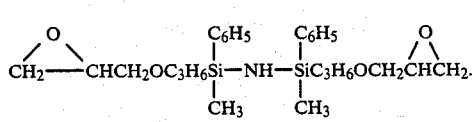

5. An epoxy group-containing disilazane, according to claim 1, wherein A is

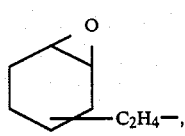

each R is a methyl group, and the epoxy group-containing disilazane has the formula,

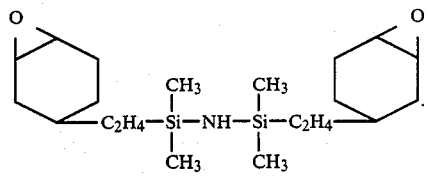

6. An epoxy group-containing disilazane, according to claim 1, wherein A is

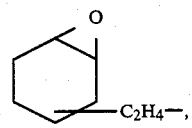

each R is a propyl group, and the epoxy group-containing disilazane has the formula,

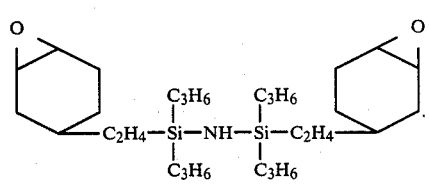

7. An epoxy group-containing disilazane, according to claim 1, wherein A is

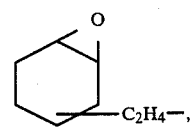

each R is a phenyl group, and the epoxy group-containing disilazane has the formula,

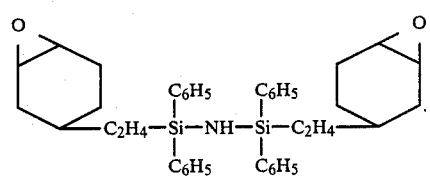

* * * * *